United States Patent [19]

Zimmerman et al.

[11] Patent Number: 5,325,728
[45] Date of Patent: Jul. 5, 1994

[54] ELECTROMAGNETIC FLOW METER

[75] Inventors: Douglas J. Zimmerman, Coon Rapids; Frank D. Dorman, Minneapolis, both of Minn.

[73] Assignee: Medtronic, Inc., Minneapolis, Minn.

[21] Appl. No.: 81,032

[22] Filed: Jun. 22, 1993

[51] Int. Cl.$^5$ ............................................. G01F 1/00
[52] U.S. Cl. ............................ 73/861.12; 73/861.11; 128/691
[58] Field of Search ........... 73/861.12, 861.15, 861.16, 73/861.17, 861.11; 128/691

[56] References Cited

U.S. PATENT DOCUMENTS

| | | | |
|---|---|---|---|
| 2,149,847 | 3/1939 | Kolin | 73/194 |
| 4,195,515 | 4/1980 | Smoll | 73/194 |
| 4,346,604 | 8/1982 | Snook et al. | 730/861.12 |
| 4,389,898 | 6/1983 | Long et al. | 73/861.12 |
| 4,741,216 | 5/1988 | Bates et al. | 73/861.12 |
| 4,784,000 | 11/1988 | Gaertner | 73/861.12 |
| 4,881,413 | 11/1989 | Georgi et al. | 730/861.12 |
| 4,899,592 | 2/1990 | Beherens | 73/861.11 |

*Primary Examiner*—Richard E. Chilcot, Jr.
*Assistant Examiner*—R. Biegel
*Attorney, Agent, or Firm*—Terry L. Wiles; Harold R. Patton

[57] ABSTRACT

An electromagnetic flow meter for measuring the flow of blood through a conduit. Flow rate is measured by applying an electromagnetic field around the conduit, with the moving electrolytic blood inducing a current that is sensed by electrodes. The flow meter includes a substantially "E"-shaped magnetic core structure as well as an "E"-shaped hinged cover piece for defining a complete flux loop. In the circuitry, a floating ground arrangement is provided for enhancing the stability and sensitivity of the meter and to ensure appropriate patient isolation. A strong magnetic field, covering the sensing region and with little flux leakage, is alternately switched in polarity. The magnetic coil driver circuit employs an arrangement of switches for facilitating very fast polarity reversal. A two-level current source in the coil current driver greatly enhances the meter's efficiency and power dissipation characteristics. Extensive provisions, both electrical and mechanical, are made to reduce the effects of capacitive coupling, spurious induced currents, electromagnetic interference, and susceptibility to noise and external magnetic fields. A dual gated sample hold circuit samples the sensor signal during steady intervals. A second dual sample-and-hold averaging circuit minimizes the effects of base-line drift in the sense signal and low-frequency noise in the amplifier stage. The flow meter includes a two section error detection circuit which generates an error signal either when the flow signal exceeds power supply limits or when the rate of change of the flow signal exceeds a clinically reasonable rate.

20 Claims, 16 Drawing Sheets

ELECTROMAGNETIC FLOW METER

FIELD OF THE INVENTION

This invention relates to the field of medical devices, and more particularly relates to an electromagnetic flow meter for measurement of liquid flow.

BACKGROUND OF THE INVENTION

The use of electromagnetic meters to measure the flow of blood or other liquids is well known. The basic concept, for example, is described in U.S. Pat. No. 2,149,847 which patent is hereby incorporated by reference. By passing blood, in a tube or other blood vessel oriented at right angles to a magnetic field, an electromagnetic force is induced in a direction mutually perpendicular to the magnetic field and the blood flow, since the blood has the property of a moving conductor cutting through a magnetic field. The voltage induced is proportional to the velocity of flow and therefore directly proportional to the volume rate of flow of the fluid. The voltage can be measured by means of electrodes positioned at diametrically opposite points of the tube along a diameter extending perpendicular to the magnetic lines of flux.

Electromagnetic flow meters of the type just described are disclosed in U.S. Pat. No. 4,195,515 to Smoll, U.S. Pat. No. 4,346,604 to Snook et al. Another example is disclosed in U.S. Pat. No. 4,881,413 to Georgi et al. entitled Blood Flow Detection Device which is hereby incorporated herein by reference in its entirety.

An important feature of all of the foregoing flow meters involves the positioning of the electrodes, the configuration of the magnetic structure, and the blood flow at a precisely fixed predetermined relationship in order to maintain an accurate calibration of the meter. In the past, it was common for the assembled tubes, electrodes, and magnetic structure to be constructed as a unitary assembly to insure proper measurement of blood flow. The unitary structure was found to have several disadvantages in the practice of medicine; in particular, such unitary construction presented problems with sterilization of the flow measuring device and with limitations on blood flow-rate sensitivity capabilities.

The above-referenced Georgi et al. '413 patent proposed an improvement to the electromagnetic flow meters wherein the conduit portion of the meter that comes directly in contact with the patient's blood was made separable from the rest of the flow detection unit. This allowed the conduit portion to be disposed of after use, or at least for the conduit portion to be separately sterilizable. However, the sliding tray arrangement used in the Georgi et al. device to support the removable flow conduit during operation of the device was difficult to manipulate and in some cases did not sufficiently secure and prevent movement of the conduit. The instability of the conduit with respect to the magnetic field generated by the device can lead to problems with zero drift stability and calibration.

The Georgi et al. '413 patent also proposed the utilization of a field focusing device permitting precise control of the electromagnetic field through which the blood flows, in order to enhance the sensitivity of the meter and minimize susceptibility to "noise" inherent in the detection system.

Notwithstanding the various advances in the technology that have been made over the years, it is the inventors' belief that there continues to be room for improvement of electromagnetic flow meters. In particular, the size and strength of the magnetic field required and the relatively low input impedance of the amplifier receiving the induced-voltage signals tend to lead to problems with zero drift stability. Also, noise susceptibility, differential rejection by the amplifier, and stray capacitance are a problem due to the placement of the input amplifier remote from the meter.

In flow meters of the type under consideration herein, the velocity of flow is sensed by the voltage generated by the moving conductive fluid in a magnetic field. To get an accurate interpretation of the total cross-section of the flow channel or flow conduit, the field must be as uniform as possible and extend along the channel for at least a distance equal to the diameter of the channel. The field must maintain a stable distribution in the sensing area when conductive or ferromagnetic material is moved around the outside of the sensor assembly. In prior art "unitary" construction flow meters, precise configuration of the magnetic field was not as difficult as with more recent flow meters having removable flow conduit sections. This is because the structure for establishing the magnetic field must be arranged to allow for insertion and removal of the disposable flow conduit. Typically, this involves providing a two-piece magnetic core structure, with one part being moveable with respect to the other. The gap between the two pieces is difficult to precisely control.

The intended application of this flow meter is to monitor the flow of blood to a patient that is undergoing open heart surgery. The flow of oxygenated blood being returned to the patient passes through the flow meter. The meter itself is part of the pump control console and has its output signal displayed to the operator of the pump so flow rate adjustments can be made as needed to maintain the patient's circulatory system.

Patient safety is the overriding concern in the design. The electric shock hazard is minimized by moving the primary isolation barrier into the flow meter itself, rather than at the signal processing circuit as is done in other blood flow meters.

SUMMARY OF THE INVENTION

In accordance with one aspect of the present invention, therefore, a electromagnetic flow meter is provided in which various components thereof have been advantageously designed and configured in a novel manner such that problems with noise susceptibility and zero drift stability are minimized and patient safety is maximized.

In accordance with another aspect of the present invention, a novel configuration of the flow meter provides for improved stability of the disposable flow conduit with respect to the magnetic field when the flow meter is assembled and closed around the insert, but which also provides for easy removal of the insert.

In accordance with another aspect of the present invention, a novel, substantially "E"-shaped core structure for creating a strong magnetic field in the sensor is provided. The "E"-shaped structure provides a large area center leg where the field passes through the removable flow conduit. The end legs of the "E"-shaped structure provide a balanced path for the field to a cover, which shunts the field around to the top of the flow conduit. In this way, the stray field outside the probe is advantageously minimized and the meter is not sensitive to external magnetic or metallic structures.

The end legs of the "E"-shaped structure are longer than the center leg, to bring the gap between the "E"-shaped structure and the cover above the sensing area. Thus, the cover has a reduced effect on the field through the sensing area, the field-producing wire coil assembly being disposed on the bottom of the flow conduit. The flux path for the sensing field is primarily in the bottom, "E"-shaped structure, minimizing the path length difference when the cover is removed. This effect makes the magnetic field in the sensing area a relatively weak function of cover placement.

In accordance with yet another aspect of the present invention, an improved magnetic coil driving circuit is provided which employs a novel switching arrangement to facilitate the rapid reversal of current through the coil. The coil driving circuit employs a high-voltage charging power supply and a lower voltage maintenance power supply. This substantially improves the efficiency and lowers the power dissipation of the meter control circuits.

In accordance with a further aspect of the present invention, the pre-amplifier is placed within the flow meter head so that the sensitive high impedance leads from the flow channel contact pin lead direct to the amplifier components on a shielded printed circuit. This pre-amplifier is supplied operating power by a commercial isolation amplifier that provides the patient an electrical isolation barrier.

In accordance with still another aspect of the present invention, components of the flow meter have been arranged and/or shielded in such a way that various effects of induction, capacitive coupling, and susceptibility to electrical noise and electromagnetic interference are minimized. The novel configuration of components also yields benefits with regard to efficiency of service for the device, and facilitates replacement of malfunctioning components in the meter. In addition, a balanced, floating ground arrangement is provided for minimizing zero drift and improving the accuracy and sensitivity of the meter.

In accordance with another aspect of the present invention, a two stage balanced synchronous demodulator circuit is used to process the flow meter pre-amplifier output into a filtered D.C. output voltage proportional to blood flow rate. These circuits are remote from the flow meter head and are connected by a cable.

BRIEF DESCRIPTION OF THE DRAWINGS

The foregoing and other features and aspects of the present invention will perhaps best be understood and appreciated with reference to a detailed description of a specific embodiment of the invention, when read in conjunction with the accompanying drawings, wherein:

FIG. 7a is a side view of the flow meter of FIGS. 1a and 1b in the closed position of FIG. 1a;

FIG. 9 is a side view showing the physical arrangement of the first and magnetic core structures from FIGS. 5a–c and 6a–c when the flow meter of FIGS. 1a and 1b is in the closed position of FIG. 1a;

DETAILED DESCRIPTION OF A SPECIFIC EMBODIMENT OF THE INVENTION

FLOW METER CONSTRUCTION

Figure 1A:
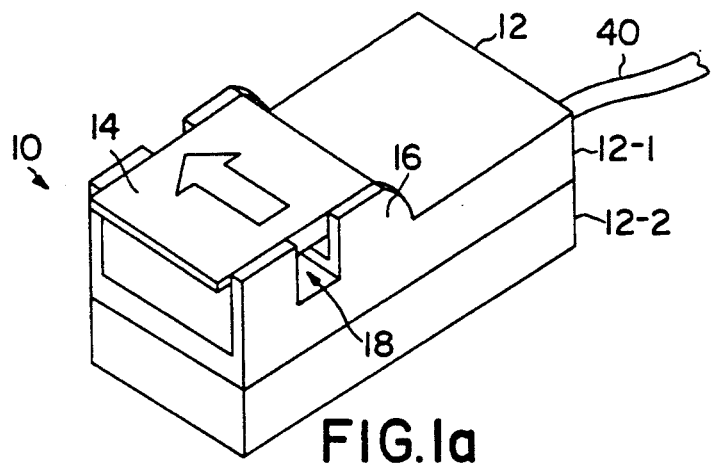
FIG. 1a is a perspective view of an electromagnetic flow meter assembly in accordance with one embodiment of the present invention.

Referring to FIG. 1a, there is shown a perspective view of an electromagnetic flow meter assembly 10 in accordance with a presently preferred embodiment of the invention. Flow meter assembly 10 comprises a base unit 12 having a cover 14 disposed on its top. Base unit 12 is a unitary structure; however, in actual implementation it may comprise upper and lower sections 12-1 and 12-2, respectively, as will hereinafter be described in greater detail. As shown in the partially exploded perspective view of FIG. 1b, hinged cover 14 is coupled to base unit 12 by means of a pin 16, allowing cover 14 to be lifted up to an open position as indicated by dashed lines 17 of FIG. 1b.

When hinged cover 14 is in the closed position depicted in FIG. 1a, a flow pathway 18 is defined through the flow meter assembly. When hinged cover 14 is lifted to the open position of FIG. 1b, flow pathway 18 is exposed from above, so that a disposable insert 20 may be received in pathway 18 as indicated by dashed lines 22 in FIG. 1b.

DISPOSABLE INSERT

Figure 2:
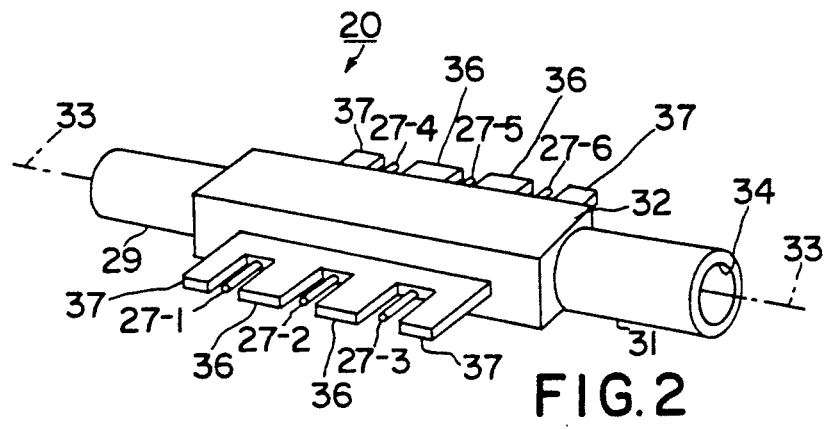
FIG. 2 is a perspective view of an insert adapted to be received in the flow channel of the flow meter of FIGS. 1a and 1b.

In FIG. 2 there is shown a more detailed perspective view of insert 20. Insert 20 is adapted to be inserted into flow channel 18 in base unit 12 so that male terminals 27 thereon engage slide terminals 28 disposed alongside flow channel 18 on top of base unit 12. Insert 20 is substantially identical to that disclosed and described in detail in the above-referenced Georgi et al. '413 patent. Insert 20 has nipples 29 and 31 extending from either end of a body portion 32. The male terminals 27-1, 27-2, 27-3, 27-4, 27-5, and 27-6 are electrical terminals which extend perpendicular to a longitudinal axis 33 which extends along a lumen 34 of insert 20. Lumen 34 extends along the entire length of insert 20 from nipple 31 through to nipple 29.

Male electrical terminals 27-1 through 27-6 are mounted in body 32 of insert 20 perpendicular to longitudinal axis 33 and, therefore, perpendicular to lumen 34 of insert 20. This relationship is more fully explained in the Georgi et al. '413 patent. Insert 20 is preferably constructed of a biocompatible plastic material such as acrylic, polyurethane, polycarbonate, or polysulfone. Preferably this material is a transparent, non-conductive and non-magnetic material for ready inspection and quality control and one that can be molded in molds commonly used for preparing such products. The different male terminals 27-1 through 27-6 have different electrical functions which may be described as comprising three functional subsets. From a mechanical point of view, male terminals 27-1 through 27-6 are mechanically positioned and imbedded in body 32 of insert 20 in exactly the same fashion. Terminals 27-2 and 27-5 comprise one functional subset and serve a different electrical function than terminals 27-1, 27-4, 27-3, and 27-6 which comprise the other two functional subsets. Terminals 27-1, 27-3, 27-4, and 27-6 are electrical terminals which provide an electrical ground for the electrical system, as is more fully described in the Georgi et al. '413 patent. Electrical male terminals 27-2 and 27-5 are designed to pick up or sense the induced voltage generated by the blood flow through lumen 34 of insert 20 as the blood moves through an electromagnetic field.

Also extending perpendicular to longitudinal axis 33 of lumen 34 are end fins 37 which also act as locators for the relative positioning of insert 20 in flow channel 18. End fins 37, however, are specifically designed to engage walls 26 disposed on base unit 12 (see FIG. 1b) to securely position insert 20 within walls 26 to prevent longitudinal movement of insert 20 along its longitudinal axis 33 when insert 20 is placed into engagement with base unit 12. Male electrical terminals 27 are designed to engage slide terminals 28 so that each pair of slide terminals 28 engage a corresponding male electrical terminal 27 when insert 20 is mounted on base unit 12.

Fins 37 are positioned on either side of body 32 and are perpendicular to body 32. Fins 37 ensure that insert 20 is properly oriented in flow channel 18 so that terminals 27-1 through 27-6 properly engage respective slide terminals 28-1 through 28-6. The fins act to physically protect male terminals 27-1 through 27-6 from mechanical damage while insert 20 is being stored or used.

All of the male terminals 27-1 through 27-6 extend perpendicular to longitudinal axis 33 of insert 20 and, therefore, perpendicular to longitudinal axis 33 of lumen 34. All terminals 27-1 through 27-6 extend into body 32 and are in electrical connection with fluid flowing through lumen 34. All terminals 27-1 through 27-6 lie in a common plane with fins 36 and 37, perpendicular to body 32 and lumen 34.

When insert 20 has been placed into engagement within base unit 12, hinged cover 14 may then be closed over insert 20, such that nipples 29 and 31 are exposed at respective ends of flow channel 18. In this position, insert 20 is held securely within an electromagnetic core structure to be hereinafter described in greater detail with reference to later figures. Blood can then be directed through insert 20 through conduits or tubes (not shown in the figures) coupled to nipples 29 and 31. In this closed position, base unit 12, hinged cover 14, and insert 20 are in a mechanical relation which permits a function of the electrical system necessary to monitor the flow of blood through insert 20. If flow meter 10 were disposed along the circulatory path of a blood pump of the type used during surgery involving the cardiovascular system, the meter can monitor the flow of blood in a patient's cardiovascular system.

As previously noted, insert 20 is substantially identical to that described in considerable detail in the Georgi '413 patent, which has been incorporated into the present disclosure by reference. Thus, no further detailed description of the construction and configuration of insert 20 is believed to be necessary herein.

MAGNETIC CORE STRUCTURE

Figure 1B:
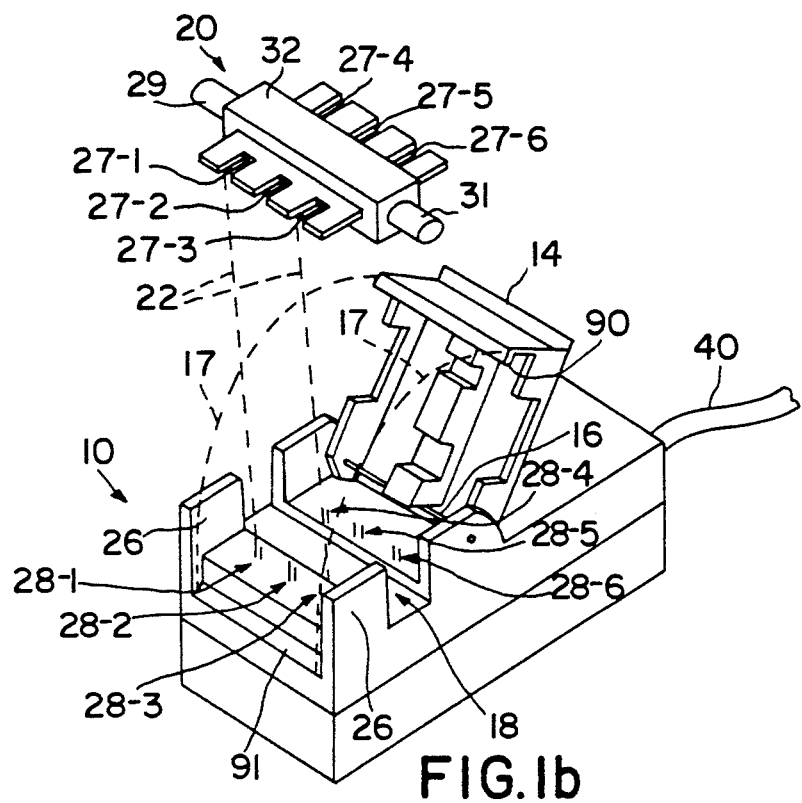
FIG. 1b is a partially exploded perspective view of the flow meter of FIG. 1a, in an open position.
Figure 3:
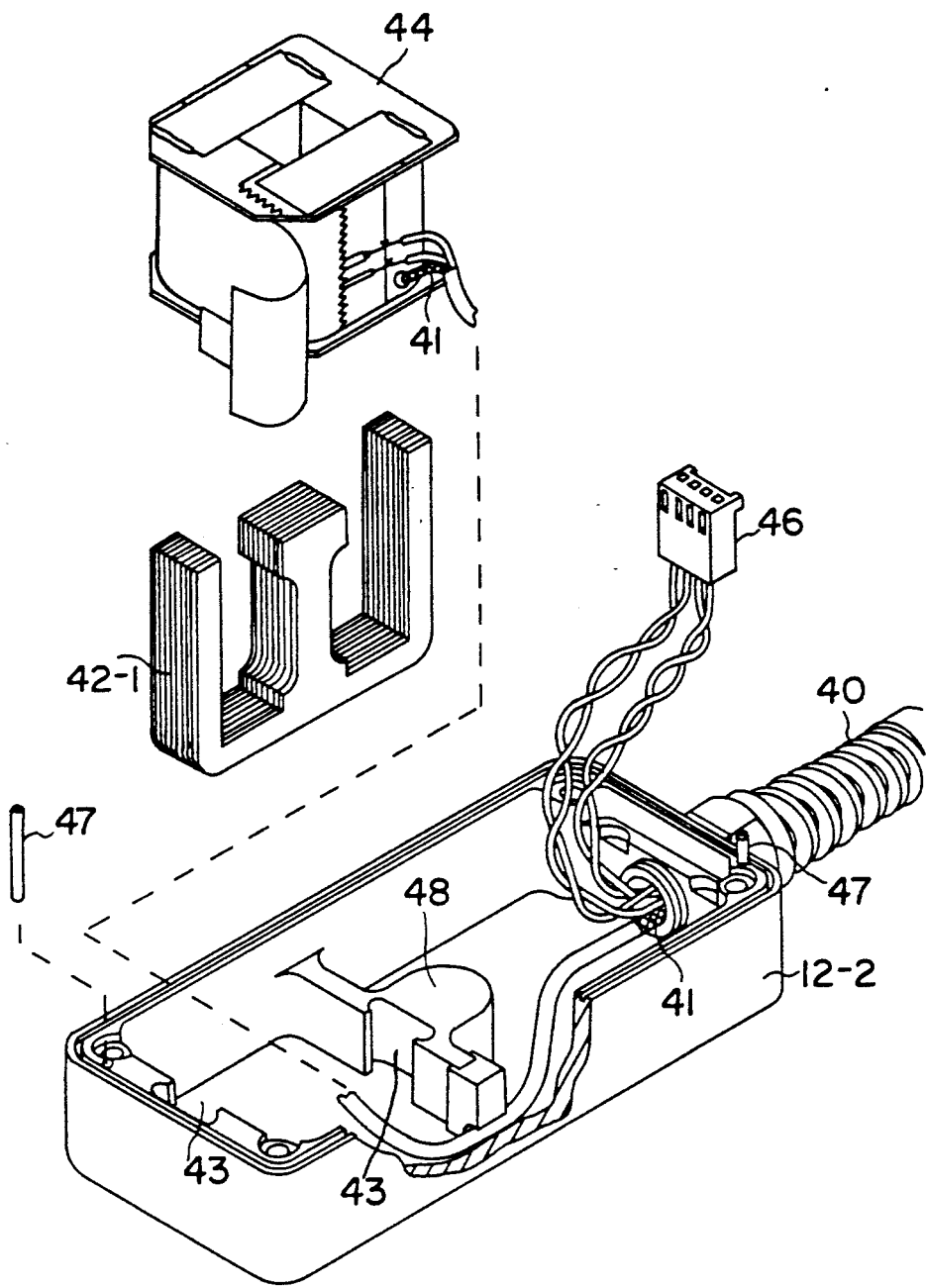
FIG. 3 is an exploded perspective view of the portion of the flow meter of FIGS. 1a and 1b.

Turning now to FIG. 3, there is shown an exploded perspective view of the bottom half 12-2 of base unit 12 shown in FIGS. 1a and 1b. Note in FIG. 3 that a multiple-conductor cable 40 extends from the back of base unit 12. As shown in FIG. 3, base unit 12, and in particular, the bottom half 12-2 thereof, is adapted to receive and support a first portion 42-1 of a two-piece magnetic core structure to be hereinafter described in greater detail. A second portion 42-2 of the magnetic core structure (this second portion not being shown in FIG. 3) is contained within hinged cover 14, as will also be hereinafter described in greater detail.

Figure 4:
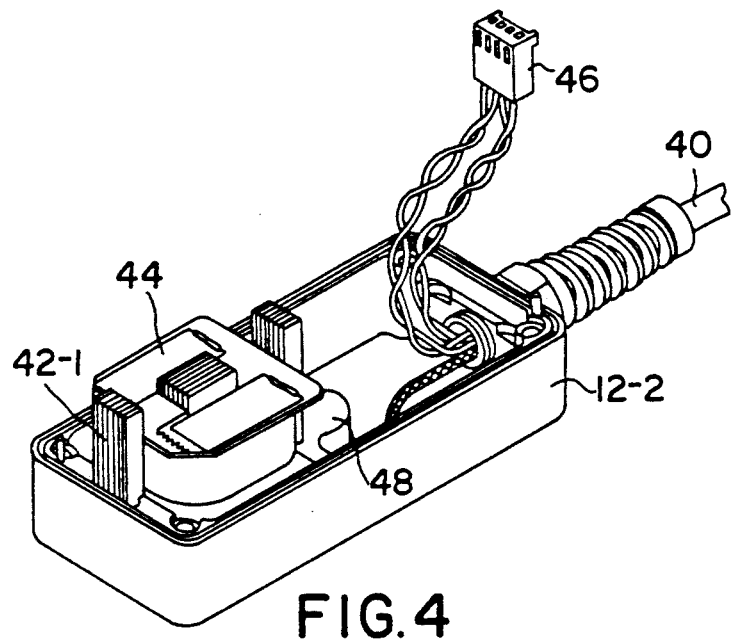
FIG. 4 is a perspective view of the portion of the flow meter from FIG. 3 shown in an assembled arrangement.

Bottom half 12-2 of base unit 12 also contains a coil assembly 44 which induces an electromagnetic field between poles of the magnetic core structure. Several wires from cable 40 are terminated with a connector 46 for facilitating connection to circuitry contained substantially in the upper half 12-1 of base unit 12, upper half 12-1 not being shown in FIG. 3. Bottom half 12-2 of base unit 12 is provided with a support member 48 for rigidly supporting magnetic core structure 42-1 and coil assembly 44 when assembled as shown in the perspective view of FIG. 4.

Figure 5A:
FIGS. 5a, 5b, and 5c are top, side, and end views of a first magnetic core structure in the flow meter of FIGS. 1a and 1b.
Figure 5B:
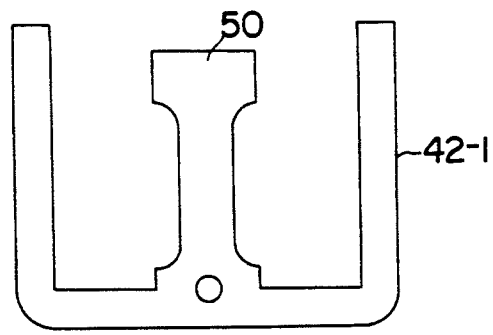
Figure 5C:
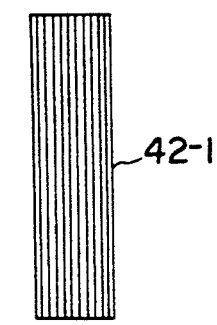
Figure 6A:
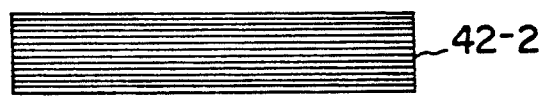
FIGS. 6a, 6b, and 6c are top, side, and end views of a second magnetic core structure in the flow meter of FIGS. 1a and 1b.
Figure 6B:
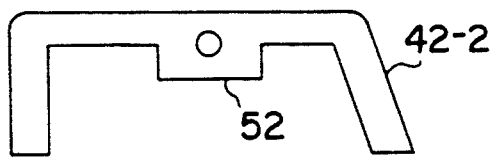
Figure 6C:
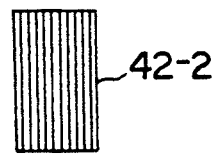

Magnetic core structure 42-1 is shown in greater detail in FIGS. 5a, 5b, and 5c, wherein FIG. 5a is a top view, FIG. 5b is a side view, and FIG. 5c is an end view. As previously noted, another magnetic core structure 42-2 is contained in hinged cover 14 of flow meter assembly 10. FIGS. 6a, 6b, and 6c are top, side, and end views, respectively, of magnetic core structure 42-2.

Figure 7A:
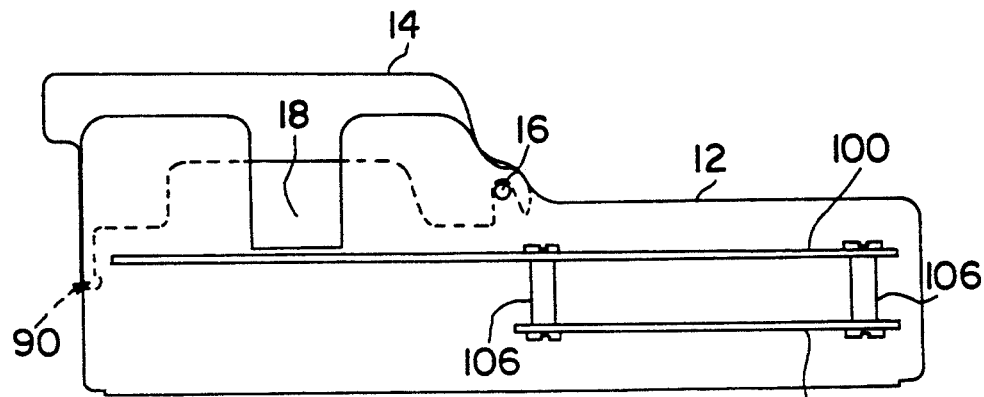
Figure 7B:
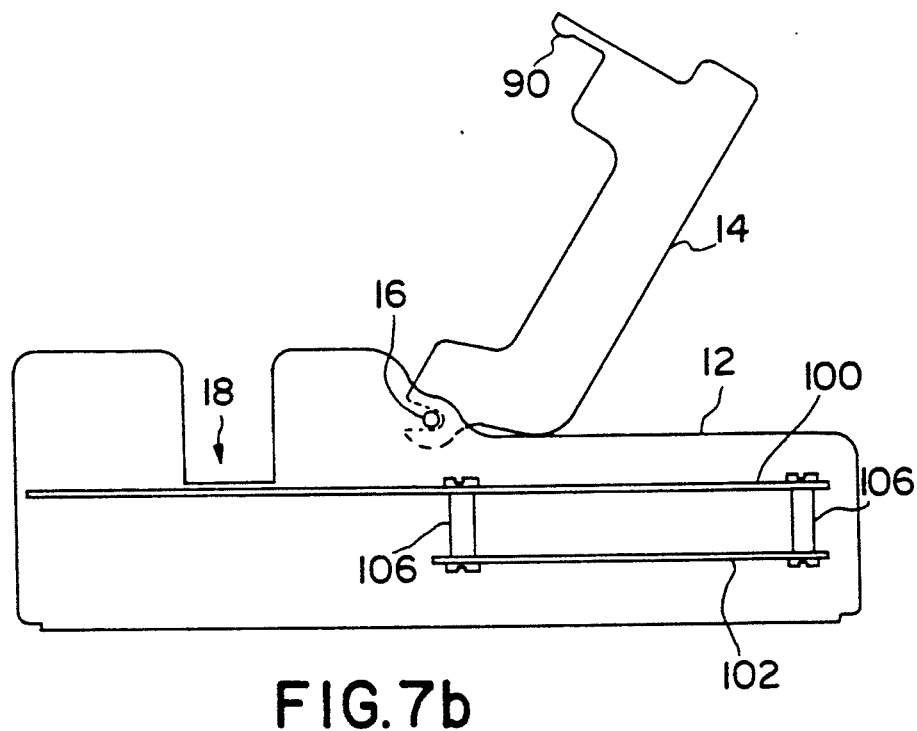
FIG. 7b is a side view of the flow meter of FIGS. 1a and 1b in the open position of FIG. 1b.

In FIG. 7a, there is shown a side view of flow meter assembly 10 with hinged cover 14 in the closed position as in FIG. 1a. In FIG. 7b, there is shown a side view of flow meter assembly 10 with hinged cover 14 in the open position as in FIG. 1b. Note from FIG. 7a that when cover 14 is closed, flow channel 18 remains open at both ends. Magnetic core structure 42-2 is disposed within cover 14 as shown in the cross-sectional view of FIG. 8. Thus, when cover 14 is in the closed position shown in FIGS. 1a and 7a, magnetic core structures 42-1 and 42-2 are brought into the physical relationship depicted in FIG. 9. Note from FIG. 9 that when cover 14 is closed, flow channel 18 is situated adjacent and directly above the center leg 50 of substantially "E"-shaped magnetic core structure 42-1, and adjacent and directly below the center leg 52 of substantially "E"-shaped magnetic core structure 42-2.

Figure 9:
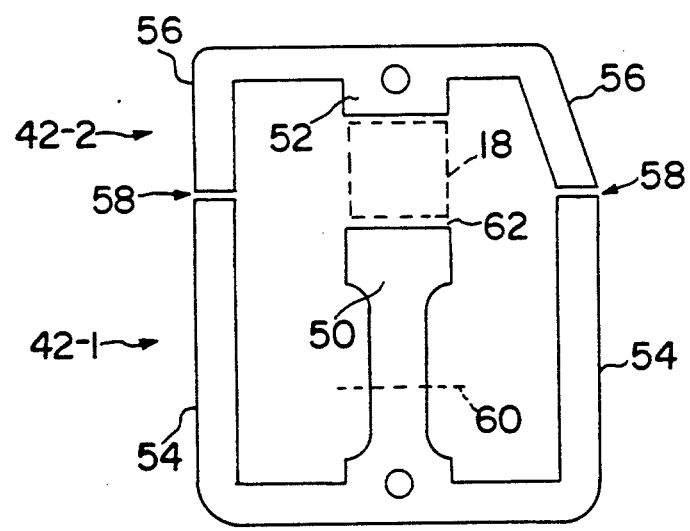

With continued reference to FIG. 9, center leg 50 of magnetic core structure 42-1 and center leg 52 of magnetic core structure 42-2 are somewhat larger than the side legs 54 of magnetic core structure 42-1 and side legs 56 of magnetic core structure 42-2, respectively. This large area provides the necessary stable distribution of magnetic field passing through insert 20 (not shown in FIG. 9) disposed in flow channel 18. End legs 54 provide a balanced path for the field to hinged cover 14 from base assembly 12. Magnetic core structure 42-2 in cover 14 shunts the magnetic field around to the top of insert 20. There is thus only a small stray field outside flow meter assembly 10. Side legs 54 of magnetic core structure 42-1 are longer than center leg 50, such that the gaps 58 between magnetic core structure 42-1 and magnetic core structure 42-2 are elevated with respect to the sensing area in flow channel 18, to bring the leg gap up to the surface of the support structure.

From FIG. 9, it will be noted that the cross section of center leg 50 of magnetic core structure 42-1, is smaller near the bottom (e.g., at dotted line 60 in FIG. 9) than at the face area (designated by reference numeral 62 in FIG. 9). This reduces the coupling of magnetic flux to the side legs and slightly reduces the total weight of the structure. The area of face 62 of center leg 50 of magnetic core structure 42-1 was determined experimentally by measuring the voltage generated at a fixed drive current and flow rate. It has been the inventors' experience that as the pole length along the flow is made smaller, the magnetic field per unit area increases and the voltage generated by the flow could also increase. The amount of coil and core structure required decreases with shorter center legs. The length chosen in the presently preferred embodiment of the invention (approximately 0.65-inches) is believed to be a suitable compromise of all of these factors. Magnetic core structures 42-1 and 42-2 are preferably made of thin lamination layers stacked and bonded with epoxy or tack welded to prevent magnetically induced vibration.

COIL ASSEMBLY

Figure 10:
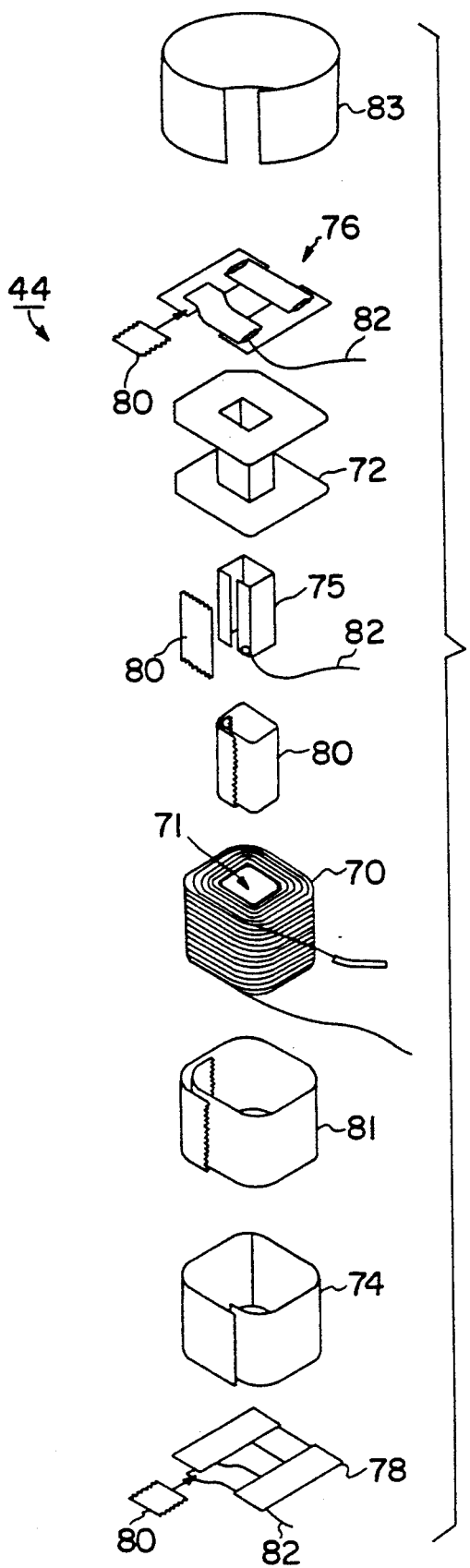
FIG. 10 is an exploded perspective view of the electromagnetic coil assembly in the flow meter of FIGS. 1a and 1b.

Turning now to FIG. 10, there is shown an exploded perspective view of coil assembly 44. The wire coil 70 for coil assembly 44 is wound on a molded plastic bobbin 72 using standard transformer methods, as would be well known to those of ordinary skill in the art. Coil assembly 44 includes 380 turns of 22 gauge wire, in order to keep the resistance as low as possible (on the order of 2.5-$\Omega$ or so). Coil assembly 44 is believed to be much larger than in prior art designs. This is possible, in part, due to the improved coil driver circuit, to be hereinafter described in greater detail. The total power loss in coil assembly 44 from a 1-Amp drive current is approximately 2.5 watts. The drive to coil assembly 44 is a high-voltage waveform that has the same phase as the flow-induced signal, which is very small. To prevent capacitive coupling of the drive signal, coil assembly 44 has electrostatic shielding, which includes conductive copper foil layers 74 and 75 on the outside and inside of coil 70, respectively, along with top and bottom shielding layers 76 and 78. Shield 74 is an electrostatic shield comprised of conductive copper foil that covers coil of wire 70 on all sides. To prevent the various shielding layers from serving as shorted turns for the magnetic field, each shield must have a gap in what would be the induced current path. Mylar tape pieces 80 are applied in the various locations shown in FIG. 10 to allow for shielding to overlap without touching. This creates the necessary gaps in the shielding layers to prevent shorted turns. Grounding wires 82 serve to couple the shielding layers to system ground. Fiberglass tape 81 protects the outer surface of coil assembly 44. The type of shielding arrangement shown in FIG. 10 is believed to be standard in isolation transformer construction.

The ferromagnetic core structure is not able to shunt all the magnetic flux produced by the coil. Therefore, a magnetic shield 83 is placed around the coil outside the electrostatic shield 74. (See FIG. 10). It must be split in the same manner as the electrostatic shield 74 to prevent a shorted turn. This shunts magnetic fields that would otherwise be affected by nearby magnetic or conductive surfaces and would distort the field passing through the insert.

Cable 40 (see FIG. 3) carries the coil drive current using a twisted-pair of wires to minimize magnetic induction from the current drive. The twisted pair is covered with a braided copper shield 41 that extends into coil shield 74 as shown in FIG. 3. In this way, there is no exposed wire within base unit 12 that can couple drive signals to the sensing electrodes in insert 20 or to sensing signal preamplifier, which shall be hereinafter described in greater detail.

The shape of flow meter 10 is apparent from FIGS. 1a, 1b, 7a and 7b. As shown in FIG. 3, magnetic core structure 42-1 is disposed in slots 43 formed in bottom portion 12-2 of base unit 12. During assembly at the time of manufacture, top portion 12-1 of base unit 12 is coupled to bottom portion 12-2 by means of insert pins 47 shown in FIG. 3. Pins 47 ensure that the two portions 12-1 and 12-2 of housing base unit 12 are held in a fixed relation; this keeps the magnetic field fixed relative to the voltage pickup electrodes in insert 20. This is believed to be an advantageous improvement over the sliding-tray arrangement disclosed in the Georgi et al. '413 patent.

Figure 8:
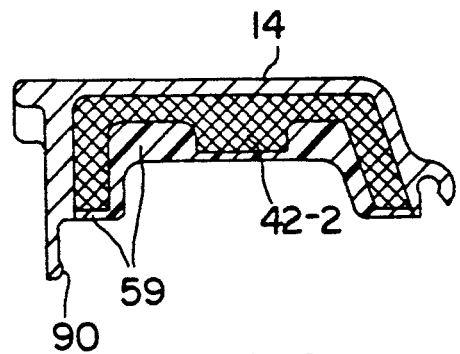
FIG. 8 is a cross-sectional view of the hinged cover of the flow meter of FIGS. 1a and 1b, including the second magnetic core structure of FIGS. 6a, 6b, and 6c.

As previously noted, to facilitate replacement of insert 20, cover 14 is hinged to permit opening as shown in FIGS. 1b and 7b. Cover 14 contains magnetic core structure 42-2, as shown in FIG. 8. As can be appreciated with reference to FIG. 9, the magnetic field flux path is substantially symmetrical, with the side legs 54 and 56 providing a return path to minimize any external field. As shown in FIG. 8, there is plastic 59 covering the ends of magnetic core structure 42-2. There is also plastic covering the ends of magnetic core structure 42-1 in base unit 12. This is necessary to keep the corrosion-prone iron alloy of the magnetic core structures 42-1 and 42-2 enclosed. The plastic at the ends of magnetic core structures 42-1 and 42-2 causes slight leakage of flux and some loss in total magnetic field strength; however, the plastic covering makes the total field less sensitive to the exact placement of cover 14 over base unit 12 when cover 14 is closed.

Cover 14 is held in the closed position by a plastic snap connection between cover 14 and base unit 12. The snap connection is implemented as a detent 90 on cover 14 which is received in a conforming groove 19 on base unit 12, as shown in FIG. 7a and in FIG. 1b. The cover can be snapped off its hinge pin for removal and cleaning.

Base unit 12 and hinged cover 14 are made of plastic or other non-metallic material strong enough to hold insert 20 and magnetic core structures 42-1 and 42-2 in rigid alignment. The sensing region between the center legs 50 and 52 of magnetic core structures 42-1 and 42-2 is about three-eighths of an inch long. To maintain the zero calibration at one part in a thousand, the positional accuracy of insert 20 must be of this same order of accuracy. Base unit 12 and cover 14 must also be strong enough to hold the heavy internal components (e.g., magnetic core structures 42-1 and 42-2 and coil assembly 44) in place when meter 10 is dropped. Meter 10 must withstand normal handling with no shift in core position. To this end, coil assembly 44 and core structure 42-1 are potted in lower housing 12-2. It is essential for terminals 27-1 through 27-6 to be precisely aligned, i.e., at right angles to the flow path and flush with the inside wall of insert 20.

PRINTED CIRCUIT BOARDS

Figure 11:
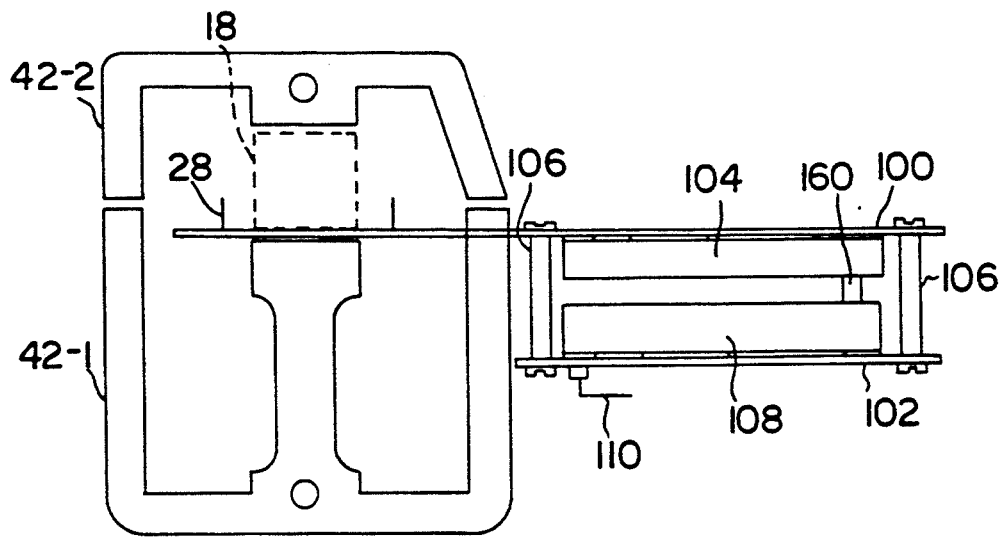
FIG. 11 is a side view showing the physical arrangement of printed circuit boards in the flow meter of FIGS. 1a and 1b.

Flow meter 10 includes printed circuit (PC) boards 100 and 102 disposed within base unit 12 as shown in FIGS. 7a and 7b. The arrangement of PC boards 100 and 102 with respect to magnetic core structures 42-1 and 42-2 is shown in the side view of FIG. 11. PC board 100 connects insert 20 in flow channel 18 to a preamplifier circuit 104. Slide terminals 28-1 through 28-6 are gold-plated steel, having a substantially hair-pin or "U" shape. Slide terminals 28-1 through 28-6 are soldered to PC board 100 such that they extend perpendicularly upward through board 100 to be exposed alongside flow channel 18 as shown in FIG. 1b and in FIG. 12. PC board 102 is coupled to board 100 via supporting and spacing members 106. PC board 102 has an amplifier 108 mounted thereon, as shown in FIG. 11. PC board 102 also has a connector 110 mounted thereon, connector 110 being adapted to be coupled to connector 46 previously shown in FIG. 3. This provides a separable connection between PC boards 100 and 102 and cable 40.

Figure 12:
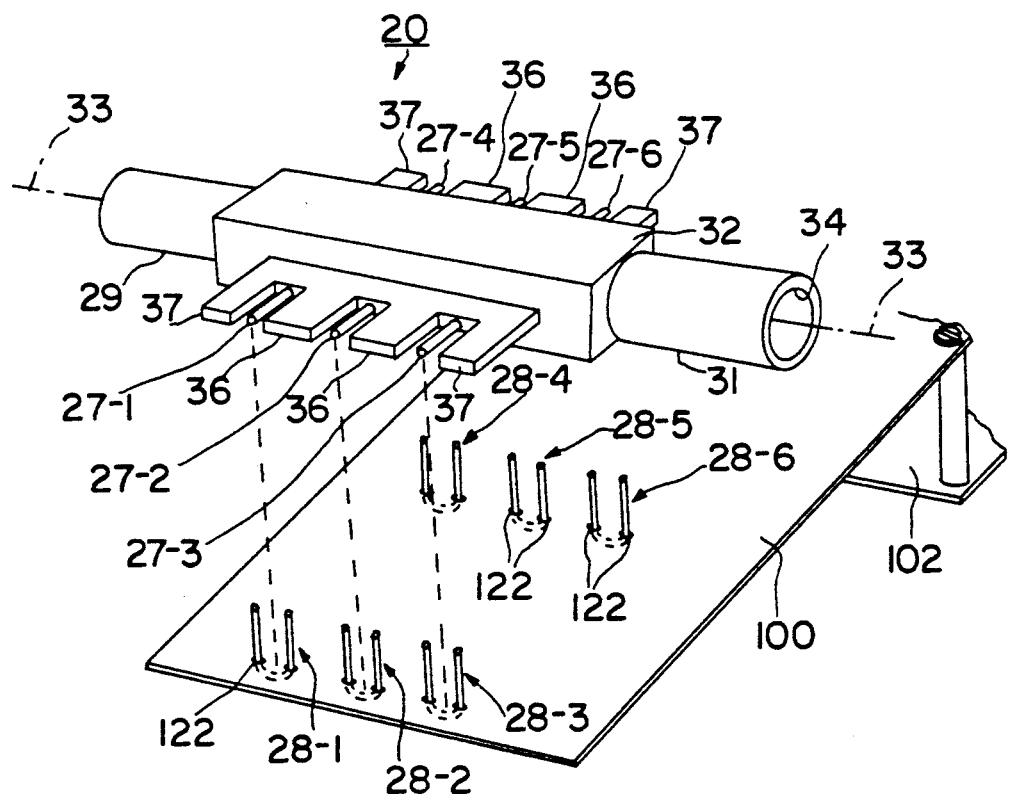
FIG. 12 is an exploded perspective view of the circuit boards of FIG. 11 and the insert of FIGS. 1b and 2.

In FIG. 12, there is shown a partially exploded perspective view of insert 20 and printed circuit board 100. Note from FIG. 12 that each of the "U"-shaped slide terminals 28-1 through 28-6 extends perpendicularly upward from board 100, being inserted into spaced-apart holes 122 in board 100 and soldered in place on the underside of board 100. When insert 20 is secured in place in flow channel 18, each of the terminals 27-1 through 27-6 engages a respective one of slide terminals 28-1 through 28-6.

Figure 13:
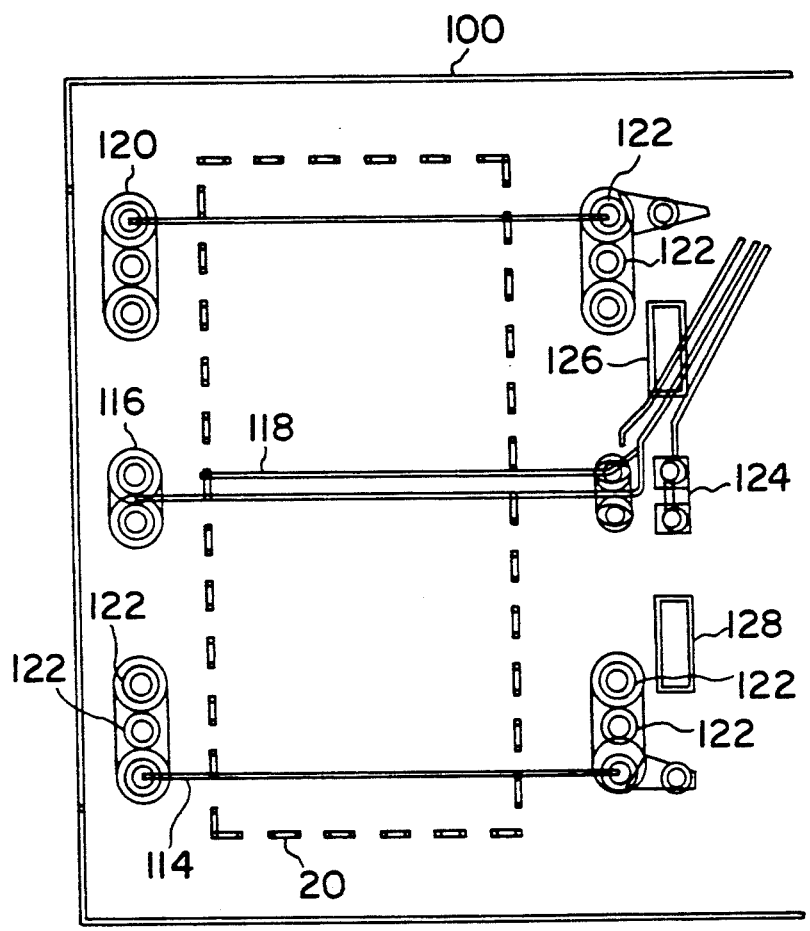
FIG. 13 is a bottom view of one of the circuit boards from FIGS. 11 and 12.

Referring now to FIG. 13, which is a top view of board 100, printed copper conductive paths 114, 116, 118, and 120 on board 100 are shown. Conductive paths 114, 116, 118, and 120 conduct signals from slide terminals 28-1 through 28-6. In particular, the ground signals on slide terminals 28-1 and 28-4 are coupled directly together by printed conductive path 120 which runs perpendicularly under insert 20 (insert 20 being shown in phantom in FIG. 13 for clarity); similarly, ground signals on slide terminals 28-3 and 28-6 are coupled together by printed conductive path 114. Slide terminal 28-2, which receives the induced voltage signal from terminal 27-2, is conducted on printed path 116 across flow channel 18 under insert 20. The placement of path 116 is critical, since it must be centered exactly under sense pins 27-2 and 27-5. As shown in FIG. 13, path 116 passes through the center of slide terminal 28-5 to maintain centering until sufficiently out of the magnetic field. Path 116 is on the top side of board 100, and is thus sandwiched between the flow-channel region of the top of base unit portion 12-1 and board 100 itself. Path 116 is thus insulated both from the blood path and magnetic core structure 42 by enough distance and plastic to resist high voltage isolation tests. The width of path 116 is narrow, on the order of 6 mil or so, to reduce capacitive coupling to core 42 and shield 74.

To balance the capacitance of both sense terminals 27-2 and 27-5, a separate dummy conductive path as a short extension of 118 on the top side of board 100 extends parallel to path 116 and is connected to sense pin 27-5. It is to be noted that path 118 leading to preamplifier 104 is on the underside of board 100, whereas path 116 is on the top side. Thus, paths 116 and 118 are at all places isolated from one another. This balances the capacitance to ground that allows preamplifier 104 to have a high rejection of 60 Hz interference that is commonly present on the blood line. This interference is minimized by the capacitance balancing features of this invention.

Printed conductive paths 116 and 118 lead away from insert 20 as a twin path, with path 116 on the top side of board 100 and path 118 on the underside of board 100. Paths 116 and 118 take a route to preamplifier 104 (FIG. 14) that is at a maximal distance from pins 27-1 through 27-6 and magnetic core structure 42. The close spacing of paths 116 and 118 (board 100 being approximately 0.020-inches thick) reduces the voltage that can be induced by the changing magnetic field. Paths 116 and 118 are thin to reduce capacitive coupling to ground.

Figure 14:
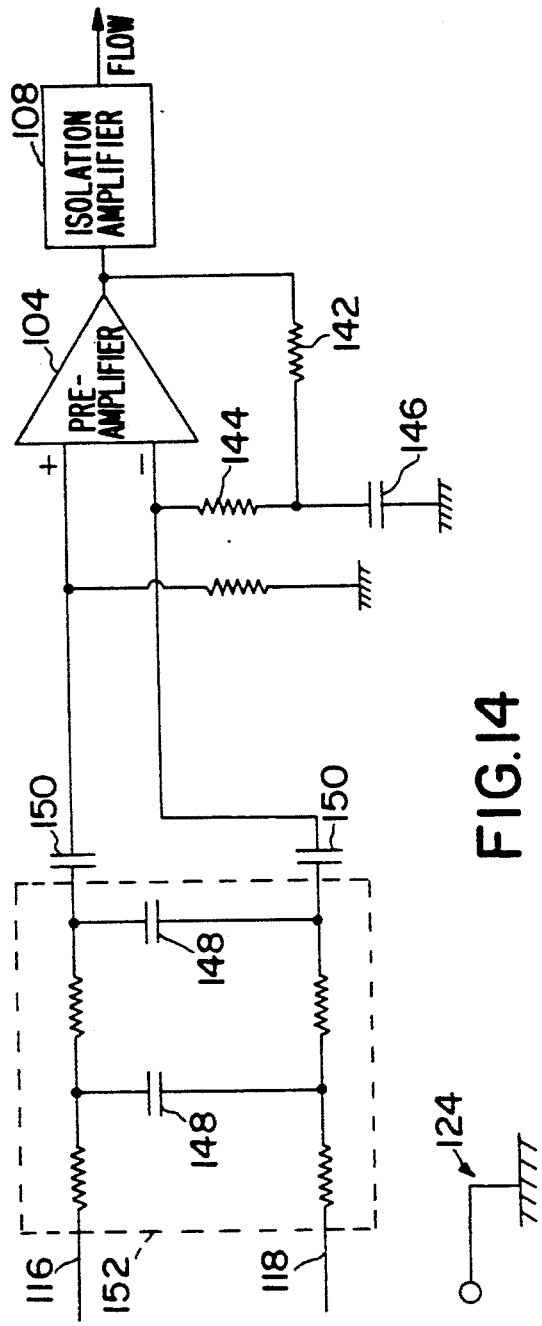
FIG. 14 is a schematic diagram of flow signal amplification circuitry in the flow meter of FIGS. 1a and 1b.

As previously noted, terminals 27-1, 27-3, 27-4, and 27-6 in insert 20 are used to connect a floating reference ground to the blood. Since there is a voltage induced in the blood by the magnetic field when it changes polarity, the ground terminals 27-1, 27-3, 27-4 and 27-6 are connected as pairs of functional subsets (a first pair being 27-1 and 27-4, and a second pair being 27-3 and 27-6) on each end of insert 20. These pairs are then connected via parallel RC networks 126 and 128 to the floating ground in preamplifier 104 (FIG. 14). This arrangement allows each ground terminal pair to go to its own potential with only a very small current flow from one end of insert 20 to the other. If all terminals 27-1, 27-3, 27-4, and 27-6 were coupled directly together, the corresponding conductive paths 114 and 120 would form an approximately $\frac{3}{4}$ turn around pole 50. This would lead to the induction of a current that would flow in the blood to complete the remaining $\frac{1}{4}$ turn. The effect of this is to balance the floating ground potential at about the same potential as the sensing pins 27-2 and 27-5, reducing the voltage pulse seen by preamplifier 104 when the magnetic field reverses polarity. In the RC networks 126 and 128 resistors are bypassed by the capacitors to extend this balanced ground drive up to high frequencies. This helps preamplifier 104 reject high-frequency signals that appear on the blood line when electrocautery equipment or the like is used on the patient.

As previously mentioned, paths 116 and 118 are small and equal in area to balance the small but important capacitive coupling to the shield ground. This capacitive coupling is part of the input impedance of preamplifier 104 and should be balanced on both paths 116 and 118 to let preamplifier 104 have high differential rejection. The capacitive coupling to floating ground is less important since the signal level from the preamplifier input leads to floating ground is much smaller than the signal-to-coil (earth) ground. The common point of networks 126 and 128 is the floating ground line 124 that shields the input lines 116, 118 on both sides of the board and on both sides of the signal lines.

SIGNAL AMPLIFICATION

Referring now to FIG. 14, there is shown a schematic diagram of a portion of the flow signal amplification circuitry in flow meter 10, including preamplifier 104 and isolation amplifier 108. In accordance with one feature of the present invention, preamplifier 104 is disposed as close as possible to insert 20, so that the high-impedance input lines to preamplifier 104 are very short, on the order of 2-inches or so. The input impedance of preamplifier circuitry can thus be kept very high.

Fixed gain, preamplifier 104 is rolled off at about 1-Hz using a feedback circuit, shown in FIG. 14 to include resistors 142 and 144 and capacitor 146. Feedback resistor 142 goes to capacitor 146 which is the reference ground point for input resistor 144. This cancels the DC offset and allows the output of preamplifier 104 to be directly coupled to isolation amplifier 108. The AC coupling is done at the input of preamplifier 104 (capacitors 150 in FIG. 14), where the impedance is high and the capacitor value can therefore be very small and still pass low frequencies.

The input of preamplifier 104 is protected from high-voltage electrocautery or defibrillation signals by a differential ladder filter 152. The differential ladder filter 152 comprises two RC filters in series. Filters 152 roll-off at approximately 10-kHz and add only about 3-kΩ into each input line. The action of filter 152 needs to be differential only since the floating ground protects the amplifier from common-mode signals. Filter 152 reduces the level of high-frequency energy that will reach preamplifier 104.

The changing magnetic field in flow meter 10 couples into all of the conductors in the region of the pole ends of core structure 42. To keep this induction pulse out of the preamplifier 104, paths 116 and 118 are routed away from the pole ends as much as possible. As a twin pair, paths 116 and 118 pick up a very small fraction of the signal as differential but have the pulse there as a common mode signal. The preamplifier input components and preamplifier 104 are placed as far away from the poles of magnetic core structure 42 as possible. Paths 116 and 118 go along the right side of board 100 to the input end of preamplifier 104 which faces the rear of base unit 12.

The output from preamplifier 104 is coupled to the input of isolation amplifier 108 via a separable connection between boards 100 and 102, the connection being designated as 160 in FIG. 11. Separable connection 160 facilitates testing of the various electronic components of flow meter 10 prior to assembly, and also allows easy field repair of the device. Isolation amplifier board 102 also has connector 110 for connecting to cable 40. Connector 110 allows top portion 12-1 of meter 10, to be separated from the bottom portion 12-2 of meter 10.

Preamplifier 104 is electrostatically shielded to prevent interference from stray fields. The shield is referenced to the floating ground of preamplifier 104.

Cable 40 couples flow meter assembly 10 to a control/display console (not shown in the figures). Cable 40 is at earth ground and does not require high-voltage protection. Isolation amplifier 108 has a passband between DC and approximately 20-kHz and provides a floating power supply to preamplifier 104.

The only parts of the flow meter assembly 10 that are at patient potential are the preamplifier board 100 and one end of the isolation amplifier board. This small volume of circuitry is easy to package and insulate to get safe patient isolation. The circuitry is inside the durable housing 12 and is therefore difficult to damage such that isolation is lost.

Isolation amplifier 108 has an adjustable gain that is set to a nominal value by external resistors and a potentiometer that allows each flow meter to be adjusted to a factory gain setting. This allows all suitable control/display consoles to have the same gain, and allows flow meter assemblies 10 to be interchanged with no adjustment to the console.

COIL DRIVER CIRCUIT

The large magnetic field generated in flow meter 10 presents a dilemma in that although the DC losses in the coil and driver circuit are low, the large inductance makes it hard to alternate the field at a high enough frequency. To get a fast field reversal during changes of polarity, the coil driver circuit must produce a high voltage to change the current direction. Preamplifier 104 and the demodulator circuit (to be hereinafter described) work best if the input signal reversals are above 100-Hz, preferably 300 or 400-Hz. Then, the low frequency 1/f noise of preamplifier 104 can be averaged out by the demodulator.

Figure 15:
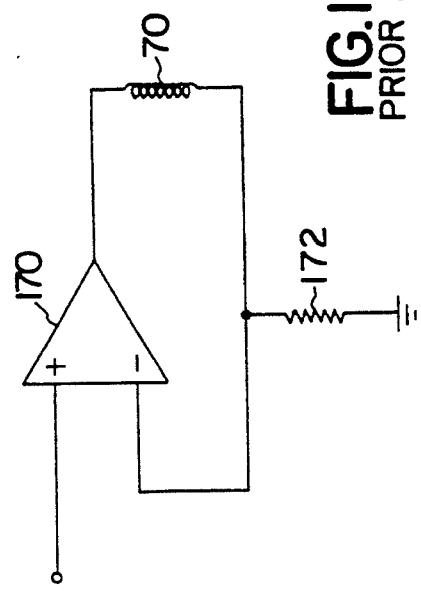
FIG. 15 is a schematic diagram of a prior art coil driver circuit.

Referring now to FIG. 15, there is shown a schematic diagram of a coil driver circuit typical of those used in the prior art. The prior art coil driver circuit of FIG. 15 includes a power operational amplifier 170 for single-ended drive, with one end of coil 70 grounded through a current sense resistor 172. As would be appreciated by those of ordinary skill in the circuit art, one problem with a current driver circuit for an inductor is that a large drive voltage is needed to reverse the current direction. Then, when the steady state current is established, the voltage drop across the low-resistance coil assembly 70 is small. The driver must therefore dissipate a large amount of power if the simple circuit of FIG. 15 is used. High supply voltages are needed for fast reversal (i.e. fast core charge). However, high current is needed to maintain the steady magnetic field for the meter. High supply voltages are not efficient at providing the high current which is needed and result in large power consumption.

Figure 16:
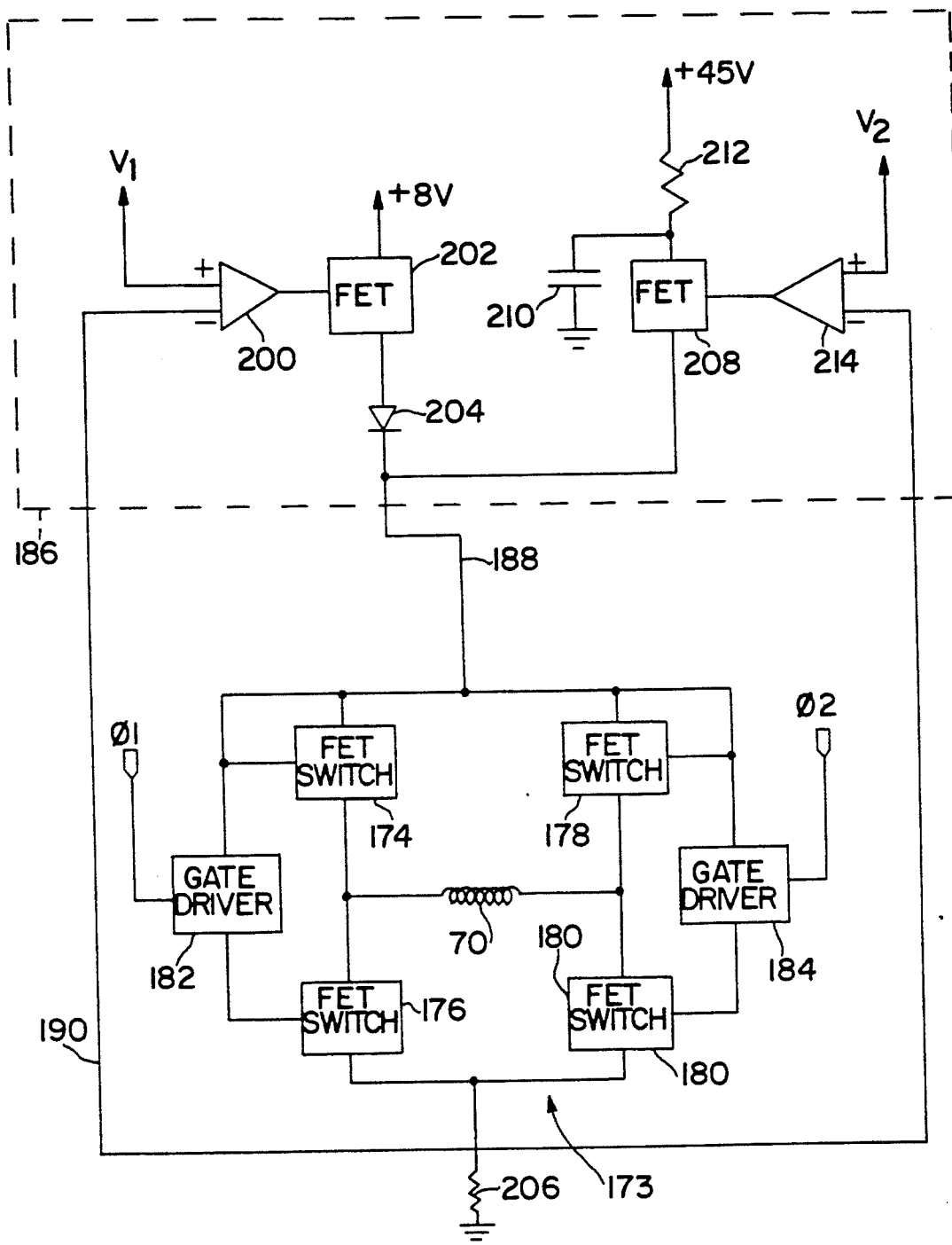
FIG. 16 is a block diagram of a coil driver circuit in the flow meter of FIGS. 1a and 1b.

To overcome the foregoing problem with the large power consumption of known high voltage coil driver circuits, the present invention includes a coil driver circuit combining the advantages of the fast coil charge time of high voltage power supplies with the high efficiency of lower voltage power supplies. The coil driver circuit uses field-effect transistor (FET) switches to reverse the current direction, and a two-level constant current source is provided, this circuit being depicted in block form in FIG. 16. The two levels comprise a first power supply voltage (+8 v) and a second high voltage supply (+45 v). In the circuit of FIG. 16, coil 70 is placed across an H-type FET bridge 173 consisting of FET switches 174, 176, 178, and 180. FET switches 174 and 176 are controlled (i.e., opened and closed) by a first gate driver circuit 182, while FET switches 178 and 180 are controlled by a second driver circuit 184. The two gate driver signals, $\phi 1$ and $\phi 2$ are 180° out of phase with respect to each other. Gate driver circuits 182, 184 provide voltage level translation from the timing source to the gates of FET's. Current for coil 70 is provided by a current source circuit 186.

With the arrangement shown in FIG. 16, current flows through coil 70 in a first direction when FET switches 174 and 180 are on (closed) and FET switches 176 and 178 are off (open), and in a second, opposite direction when FET switches 174 and 180 are off and FET switches 176 and 178 are on. In either case, current is provided by current source 186, the current flowing from current source 186 on conductor 188, through coil 70 in either direction. Thus, coil current can be reversed while the current input and output terminals of H-bridge 173 stay the same.

The current source 186 is detailed in FIG. 16. Current source 186 is a low voltage, high current source which consists of operational amplifier 200, FET 202 and Diode 204. The current that passes through the H bridge 173 goes to ground through resistor 206. The voltage developed across this resistor is proportional to the current. This voltage returns to the negative input of the operational amplifier 200 as negative feedback. The operational amplifier 200 output drives a power FET 202 to place a voltage on the bridge that drives the feedback voltage to coincide with a first input reference voltage $V_1$. This circuit thus maintains the current through the coil at a fixed value independent of the voltage drops through the bridge components and the flowmeter coil 44.

When the gate driver circuits 182, 184 reverse the current direction through the coil 70, the stored magnetic field of the coil induces a large increase in voltage at the top of the bridge as the current tries to reverse. This voltage is blocked by diode 204 and the current passes through the reverse protection diode in FET 208 to a storage capacitor 210. Part of the energy needed to reverse the magnetic field direction comes from this stored energy in capacitor 210.

The reverse current flow also flows in resistor 206 and causes the feedback voltage to go negative. This turns both operational amplifiers 200 and 214 on, but only has an effect on operational amplifier 214 since the voltage on top of the bridge is more positive than the +8 volt power supply of FET 202. Operational amplifier 214 turns on FET 208, which connects the bridge to capacitor 210 which is kept charged by the +45 volt power supply through resistor 212.

The level of a second input reference voltage $V_2$ is set at a desired percentage of the level of $V_1$. This enables the coil driver circuit to achieve the fast coil charge time provided by the high voltage power supply (+45 v) and the high efficiency (lower power consumption) of the low voltage power supply (+8 v) in maintaining the needed high current. In the preferred embodiment, $V_2$ is set at about 80% of the level of $V_1$. Thus, in operation when the coil 70 has been charged to within 80% of the set point by FET 208, FET 202 takes over to bring the current up to the maximum. In the preferred embodiment the set point current is 1 amp, and the sense resistor is 0.5Ω. The total circuit power dissipation of this coil driver circuit is approximately ⅓ of comparable prior art devices.

OUTPUT SIGNAL DEMODULATION CIRCUIT

The output signal from flow meter 10 in accordance with the presently disclosed embodiment of the invention (i.e., the output signal "FLOW" from isolation amplifier 108 —see FIG. 14) is a square wave signal that also contains substantial broad-band noise, due to such factors as the high gain (on the order of 1000×) and relatively high impedance of the input electrodes (5- to 50-kΩ). There is also base line drift from preamplifier 104 since the output is DC coupled.

Figure 17:
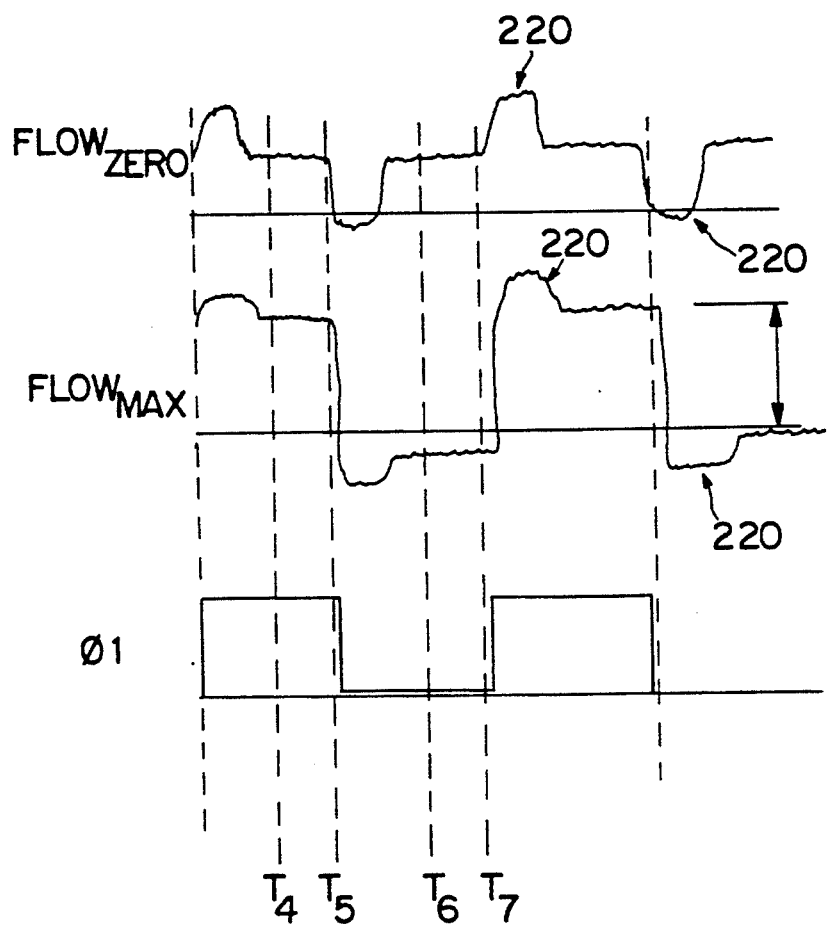
FIG. 17 is a diagram showing voltage wave forms at the demodulator input of FIG. 15.

The reversing DC drive to coil 70 produces an output voltage proportional to the average flow velocity of blood through insert 20. The output voltage waveform would be the same as the driver current waveform if there were no inductive effects. The effect seen by preamplifier 104 is an impulse in voltage during the reversal of current. This impulse can be of either polarity depending upon the exact position of pins 27 in the particular insert 20 used and the impedance of the individual pins. Typical "FLOW" signals are shown in FIG. 17. In FIG. 17, the signal designated "FLOW$_{zero}$" corresponds to the output of isolation amplifier 108 when there is no flow through insert 20; "FLOW$_{max}$" corresponds to the output signal resulting from maximum flow through insert 20.

The AC component of the "FLOW" signal is extracted by synchronous demodulation using the coil drive signal $\phi 1$ (and/or its counterpart $\phi 2$) as a reference frequency. The signal is sampled for no more than the last half of each magnetic field polarity cycle, to reject the aforementioned large spurious spikes of voltage (designated generally as 220 in FIG. 17) generated by coil polarity reversal during the early part of each polarity cycle. Thus, in FIG. 17, one sampling interval is between times $T_1$ and $T_2$, and another is between $T_3$ and $T_4$.

Figure 18:
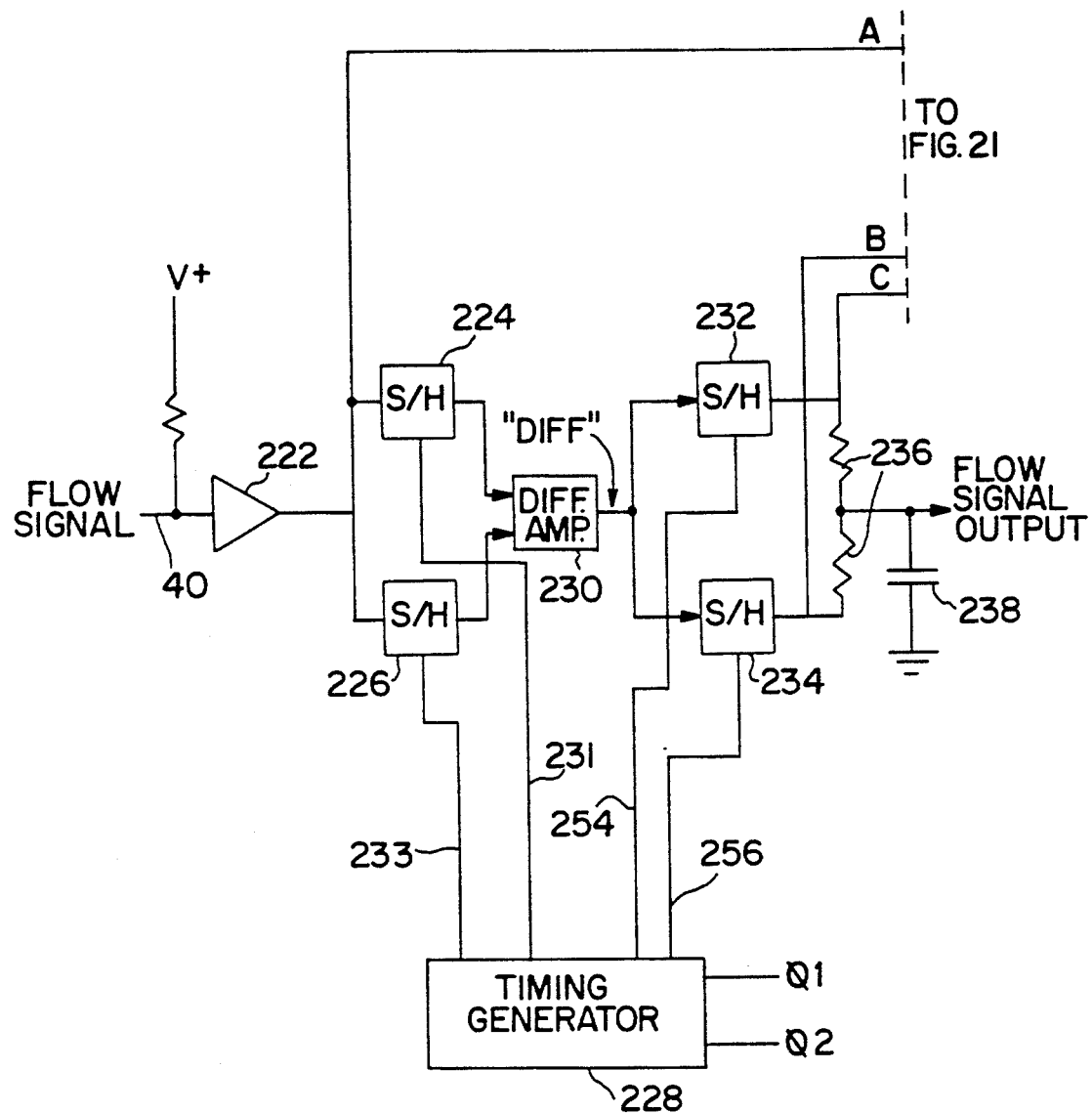
FIG. 18 is a schematic diagram of the synchronous demodulation circuit in the flow meter of FIGS. 1a and 1b.

FIG. 18 is a block diagram of the synchronous demodulation circuit used to extract the flow value from the previously described waveforms. An amplifier 222 receives the flow signal on cable 40 and brings the signal up to a level appropriate for the demodulation process. Two identical sample-hold circuits 224 and 226 are gated on alternate cycles by logic drive signals from a timing generator 228. All timing and switching signals are generated by this circuit.

The flow rate is represented by the difference between the voltage values held by the two sample-hold circuits, 224 and 226. A precision difference amplifier 230 is used to extract the output value difference between the sample-hold circuit, 224 and 226. The output of the difference amplifier 230 is proportional to flow.

The output signal of amplifier 230 could be used directly as the output from flow meter 10, except for the effect of low frequency base-line noise of the "FLOW" signal provided to the sample-hold circuits 224, 226. When the input to the sample-hold circuits 224, 226 are exposed to low frequency noise the effect is to produce an error signal which is caused by the delay in sampling time between the sample-hold circuits.

Figure 19A:
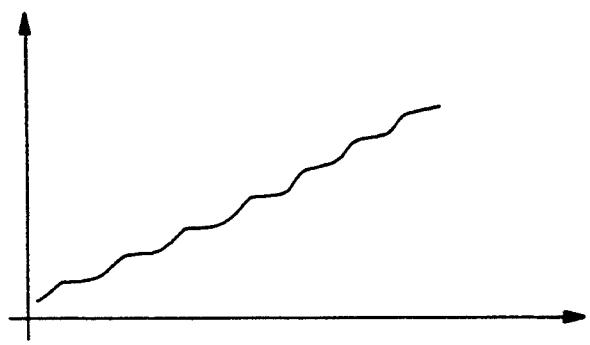
FIGS. 19a, 19b, and 19c are diagrams showing voltage waveforms of signals present in the gated integrator circuit of FIG. 18.
Figure 19B:
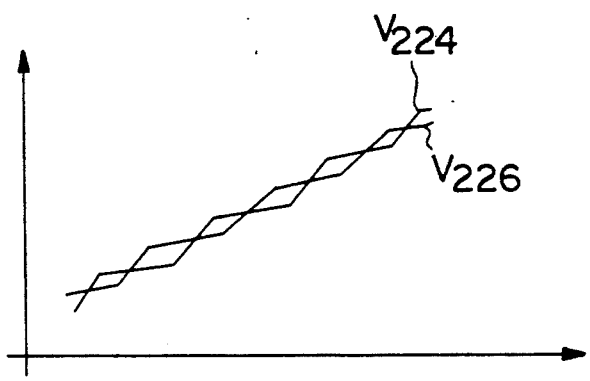

The output from each sample-hold circuit (224 and 226) ramps up when the corresponding sample and hold circuit is on. A typical output signal from sample-hold circuit 224 or from sample-hold circuit 226 is shown in FIG. 19a. Thus, when one sample-hold circuit is on, its output level overtakes the output level of the other, which will be holding its last sample, taken at a lower voltage (assuming an up-ramp in input voltage; the opposite would be true for decreasing input voltage). The alternate overtaking of one sample-hold output signal by the other is depicted in FIG. 19b, wherein the output from sample-hold circuit 224 is designated as $V_{224}$ and the output from sample-hold circuit 226 is designated $V_{226}$.

Figure 19C:
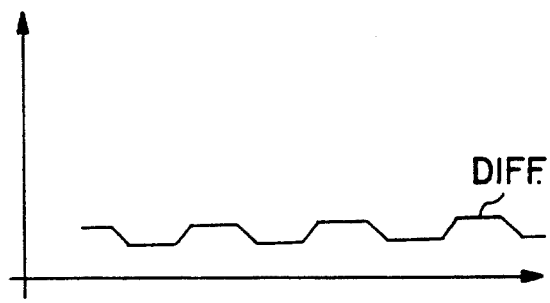

In FIG. 19c, the output signal "DIFF" from difference amplifier 230 is shown. The true output of flow meter 10 is then the average of the "DIFF" signal. In order to achieve this averaging of the "DIFF" signal, a second pair of sample-hold circuits 232 and 234 are used to alternately sample and average the "DIFF" signal. Such averaging cancels the first order effects of ramp signals from sample-hold circuits 224 and 226, which resulted from low-frequency noise of preamplifier 104.

Figure 20:
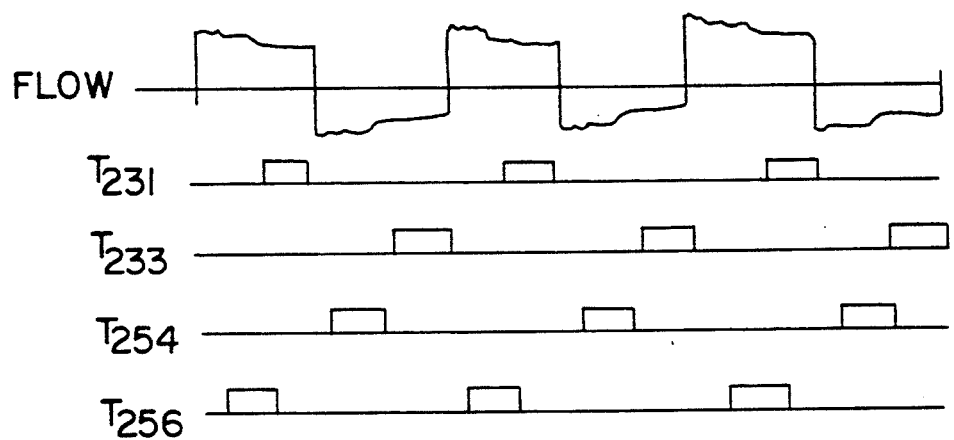
FIG. 20 is a timing diagram which shows the relationship between the timing generator outputs 238 in reference to the flow signal 40 of FIG. 18.

With continued reference to FIG. 18, a sample-hold averaging circuit in accordance with the presently disclosed embodiment of the invention is shown. The sample-hold circuits, 232 and 234, are gated to read the "DIFF" output from difference amplifier 230 after each sample-hold circuit sampling period. The timing generator 228 controls sample-hold circuits 232 and 234 to achieve the desired sampling intervals. In particular, timing generator 228 generates a first signal on line 254 to activate sample-hold circuit 232, and a second signal on line 256 to activate sample-hold circuit 234. The timing diagram of FIG. 20 shows the signals on lines 254 and 256 (designated $T_{254}$ and $T_{256}$, respectively) in relation to the sample control signals $T_{231}$ and $T_{233}$ conducted on lines 231 and 233, respectively, to control sample and hold circuits 224 and 226, respectively.

The output of the two sample-hold circuits 232 and 234 are averaged using a resistive divider 236 across their output terminals. The signal is filtered at this point by a capacitor 238 to ground. Additional circuitry (not shown) not pertinent to the present invention is used to buffer and offset the flow signal voltage for presentation to appropriate display circuitry.

ERROR DETECTION CIRCUIT

During surgery when the flowmeter is used in a blood line that leads to the patient large electrical disturbances can be generated in the flow meter electronics by the use of electrocautery devices. These devices consist of probes used to stop blood leakage from small vessels during surgery. They generate high voltage RF signals that pass through the blood lines directly into the flow meter input as well as being radiated as RF signals.

These signals can exceed the rejection limits of the filter circuits described earlier and cause the flow meter circuitry to saturate. During saturation the flow signal output is inaccurate. In order to notify the system operator of the inaccurate reading, circuitry has been added which will detect and inform the operator, either audibly or visually, of an error condition.

Figure 21:
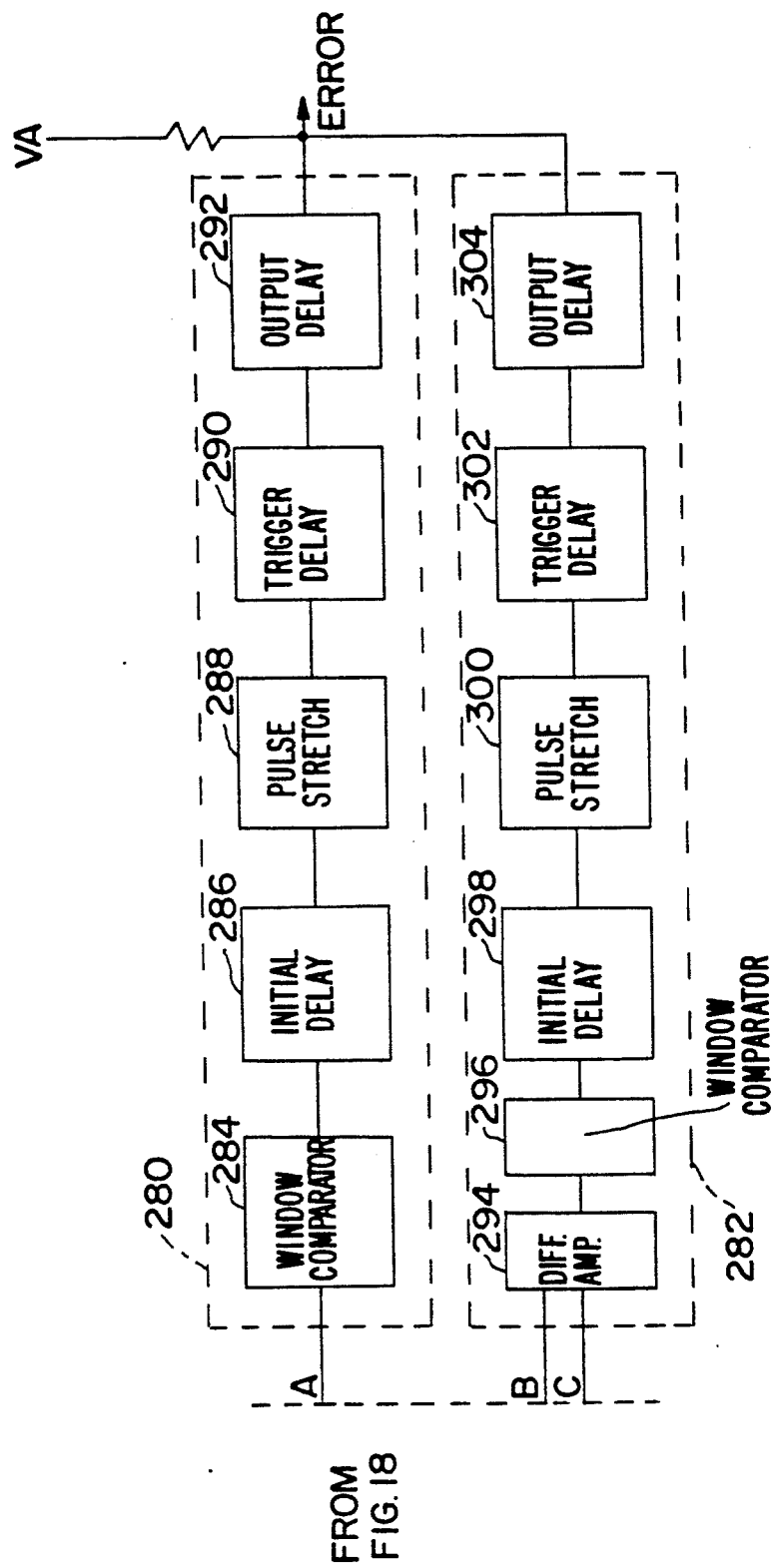
FIG. 21 is a block diagram of the error detection circuit utilized in the present invention.

FIG. 21 is a block diagram of the error detection circuitry utilized in the present invention. The error detection circuitry is divided into two sections, a rail detector (280) and a noise detector (282).

The rail detector 280 is used to detect conditions when the flow signal may be compromised due to signals approaching power supply limits. It includes circuitry to prevent false triggering of the error detector logic. In operation of the rail detector 280, the flow signal (A) from amplifier 222 (FIG. 18) is applied to window comparator 284. The window comparator 284 provides an active output anytime the signal exceeds the window comparator limits. The limits are selected to be compatible with the power supply limits. In the preferred embodiment disclosed herein the limits are about ±10 v. The output of window comparator 284 is applied to initial delay circuit 286 which provides a short qualification delay. The initial delay circuit 286 prevents very short interfering signals, which have no consequences to the operator, from triggering the rail detector circuit 280. The output of the initial delay circuit 286 is applied to pulse stretch circuit 288. The pulse stretch circuit 288 is used to combine separate pulses from initial delay circuit 286 into a single pulse. This allows the detection of burst type interference. The output of pulse stretch circuit 288 is applied to the trigger delay circuit 290. The trigger delay 290 provides an output anytime the interfering signal is present long enough to compromise the flow signal output. The output of trigger delay 290 is applied to the output delay circuit 292. The output delay circuit 292 provides an output anytime the input from the trigger delay circuit 290 is active. The output remains active for a finite time period after the trigger delay circuit 290 input has become inactive. This allows the flow signal time to recover from the interference. The output of the output delay circuit 292 is combined with the output of the noise detector circuit 282 to provide an error output signal.

The noise detector 282 is used to detect conditions when the flow signal is changing faster than is clinically reasonable. This is determined by comparing two adjacent flow samples. If the difference between the samples exceeds a preset limit, an error signal is produced. In operation of the noise detector 282, the adjacent flow samples (B and C) are provided from sample-hold circuits 232 and 234 (from FIG. 18) and applied to difference amplifier 294. The output of difference amplifier 294 is proportional to the change in flow per unit time. If this value exceeds a predetermined limit, an error is reported. The output of the difference amplifier 294 is applied to a window comparator 296 and delay circuitry 298, 300, 302 and 304 which is similar in operation to the corresponding delay circuitry provided for the rail detector 280. The output of the output delay circuit 304 is combined with the output of the rail detector circuit 280 as a "wired or" connection to provide an error output signal which is converted to an audio or visual alarm.

What is claimed is:
1. An apparatus for measuring fluid flow, comprising;
a base unit assembly having a cover piece coupled to an upper surface thereof, said base unit and cover piece defining a lateral flow channel therebetween, said cover piece being moveable from an open position in which said flow channel is exposed from above, to a closed position in which said cover piece defines a top of said flow channel;
a tubular insert, adapted to be received in said flow channel, said insert being further adapted to be connected at its ends to a fluid flow circuit such that said fluid flows through said insert;
a plurality of sensing electrodes, extending into said tubular insert and terminating on an inner surface thereof;
a plurality of connectors, projecting upward out of said upper surface of said base unit and adapted to engage said sensing electrodes when said tubular insert is secured in said flow channel;

a first, substantially "E" shaped magnetic core structure having first and second side legs and a center leg, said first magnetic core structure being disposed in said base unit assembly such that said center leg is disposed adjacent said flow channel;

a second, substantially "E" shaped magnetic core structure having first and second side legs and a center leg, said second magnetic core structure being disposed in said cover piece such that when said cover piece is in said closed position, said center leg is disposed adjacent said flow channel, a central portion of said flow channel being thereby disposed within a gap between said center legs of said first and second magnetic core structures; and a wire coil assembly having first and second electrical terminals, said coil assembly disposed around said center leg of said first magnetic core structure and responsive to an electrical coil driver signal to establish a uniform magnetic field in said central portion of said flow channel between said center legs of said first and second magnetic core structures.

2. An apparatus in accordance with claim 1 wherein said cover piece is coupled to said upper surface by a hinge.

3. An apparatus in accordance with claim 1 wherein said tubular insert is secured in said flow channel by said cover piece in said closed position.

4. An apparatus in accordance with claim 1 wherein said plurality of sensing electrodes terminate on said inner surface of said tubular insert at diametrically opposite points in a common transverse plane.

5. An apparatus in accordance with claim 1 wherein said first and second side legs of said first substantially "E" shaped magnetic core structure are longer than said center leg of said first substantially "E" shaped magnetic core structure.

6. An apparatus in accordance with claim 1 wherein said first and second side legs of said second substantially "E" shaped magnetic core structure are longer than said center leg of said second substantially "E" shaped magnetic core structure.

7. An apparatus in accordance with claim 1, further comprising a coil driver circuit for charging said coil assembly to a predetermined set point current, said coil driver circuit being coupled to said first and second electrical terminals of said coil assembly, said coil driver circuit comprising:

a constant current source including a first voltage source and a second higher level voltage source, means for switching between said first and second voltage sources to generate said electrical coil driver signal, such that said second higher level voltage source is activated to charge said coil assembly up to a level equal to a predetermined portion of said set point current at which level said first voltage source is activated to charge said coil assembly the rest of the way to said set point current and to maintain said set point current.

8. An apparatus in accordance with claim 1 further including an output signal demodulation circuit, the output signal being indicative of the flow of fluid, the output demodulation circuit comprising:

means for generating timing signals, first means responsive to said timing signals for taking at least two samples of the magnitude of the voltage of the output signal, means responsive to said first sampling means for generating a difference signal indicative of the difference between the voltage magnitude of said at least two samples, such that said difference signal represents the rate of fluid flow with the alternating current component of the output signal having been extracted.

9. An apparatus in accordance with claim 8 wherein said output signal demodulation circuit further includes:

second means responsive to said timing signals for taking at least two samples of said difference signal; and means for generating a fluid flow signal indicative of the average of said at least two samples of said difference signal.

10. An apparatus in accordance with claim 1 further including an error detection circuit for detecting error conditions in the fluid flow signal generated by the apparatus, the error detection circuit comprising:

rail detector means for generating a first error signal when the fluid signal magnitude levels approach power supply limits, and noise detector means for generating a second error signal when the fluid flow signal changes faster than a predetermined limit.

11. An apparatus for measuring the flow of blood, comprising:

a base unit assembly having a hinged cover piece coupled to an upper surface thereof, said base unit and hinged cover piece defining a lateral flow channel therebetween, said hinged cover piece being moveable from an open position in which said flow channel is exposed from above, to a closed position in which said cover piece defines a top of said flow channel;

a tubular insert, adapted to be received in said flow channel and secured therein by said cover piece in said closed position, said insert being further adapted to be connected at its ends to an extracorporeal blood circuit such that said blood flows through said insert;

a plurality of sensing electrodes, extending into said tubular insert and terminating on an inner surface thereof at diametrically opposite points in a common transverse plane;

a plurality of connectors, projecting upward out of said upper surface of said base unit and adapted to engage said sensing electrodes when said tubular insert is secured in said flow channel by said cover piece;

a first, substantially "E" shaped magnetic core structure having first and second side legs and a center leg, said first magnetic core structure being disposed in said base unit assembly such that said first and second side legs and said center leg extend upward and such that said center leg is disposed beneath said flow channel;

a second, substantially "E" shaped magnetic core structure having first and second side legs and a center leg, said second magnetic core structure being disposed in said cover piece such that when said cover piece is in said closed position, said first and second side legs and said center leg thereof project downward and such that said center leg is disposed above said flow channel, a central portion of said flow channel being thereby disposed within a gap between said center legs of said first and second magnetic core structures; and a wire core assembly having first and second electrical terminals, said coil assembly disposed around said center leg of said first magnetic core structure and responsive to an electrical coil driver signal to establish a uniform magnetic field in said central portion of said flow channel between said center legs of said first and second magnetic core structures.

12. An apparatus in accordance with claim 11, further comprising:

a printed circuit board, horizontally disposed within said base unit assembly such that a portion of said printed circuit board is disposed beneath said flow channel and above said center leg of said first magnetic core structure, said printed circuit board being electrically coupled to said plurality of connectors to receive electrical flow signals sensed by said plurality of electrodes; and said printed circuit board having separate electrically conductive paths for conducting said electrical flow signals in a capacitively balanced manner.

13. An apparatus in accordance with claim 12 wherein said separate electrically conductive paths are disposed on opposite sides of said printed circuit board.

14. An apparatus in accordance with claim 12, wherein:

said plurality of said sensing electrodes comprise a first subset disposed proximal to one end of said insert and a second subset disposed proximal to an opposite end of said insert, said first and second subsets being electrically coupled to a common node via at least one resistor, said common node thereby providing a floating ground signal; and said plurality of sensing electrodes comprise a third subset disposed substantially centrally on said insert, said third subset comprising first and second diametrically opposite electrodes for sensing voltage induced by said flow of blood through said insert.

15. An apparatus in accordance with claim 14, wherein:

said first electrode of said third subset is coupled via one of said electrical connectors to a first conductive path disposed on a first side of said printed circuit board; and said second electrode of said third subset is coupled via another one of said electrical connectors to a second conductive path disposed on a second side of said printed circuit board; such that capacitance between said first conductive path and said second conductive path is balanced.

16. An apparatus in accordance with claim 15, wherein said first and second conductive paths extend in alignment beneath said flow channel.

17. An apparatus in accordance with claim 11, further comprising a coil driver circuit for charging said coil assembly to a predetermined set point current, said coil driver circuit being coupled to said first and second electrical terminals of said coil assembly, said coil driver circuit comprising:

a constant current source including a first voltage source and a second higher level voltage source, means for switching between said first and second voltage sources to generate said electrical coil driver signal, such that said second higher level voltage source is activated to charge said coil assembly up to a level equal to a predetermined portion of said set point current at which level said first voltage source is activated to charge said coil assembly the rest of the way to said set point current and to maintain said set point current.

18. An apparatus in accordance with claim 11 further including an output signal demodulation circuit, the output signal being indicative of the flow of blood, the output signal demodulation circuit comprising:

means for generating timing signals, first means responsive to said timing signals for taking at least two samples of the magnitude of the voltage of the output signal, means responsive to said first sampling means for generating a difference signal indicative of the difference between the voltage magnitude of said at least two samples, such that said difference signal represents the rate of blood flow with the alternating current component of the output signal having been extracted.

19. An apparatus in accordance with claim 18 wherein said output signal demodulation circuit further includes:

second means responsive to said timing signals for taking at least two samples of said difference signal; and . means for generating a blood flow signal indicative of the average of said at least two samples of said difference signal.

20. An apparatus in accordance with claim 11 further including an error detection circuit for detecting error conditions in a blood flow signal generated by the apparatus, the error detection circuit comprising:

rail detector means for generating a first error signal when the blood signal magnitude level approaches power supply limits, and noise detector means for generating a second error signal when the blood flow signal changes faster than a predetermined limit.

* * * * *